US010538480B2

(12) United States Patent
Arras et al.

(10) Patent No.: US 10,538,480 B2
(45) Date of Patent: Jan. 21, 2020

(54) PROCESS FOR THE PRODUCTION OF DI- AND POLYAMINES OF THE DIPHENYLMETHANE SERIES

(71) Applicant: Covestro Deutschland AG, Leverkusen (DE)

(72) Inventors: Jürgen Arras, Itzehoe (DE); Tobias Cäsar Keller, Holziken (CH); Javier Pérez-Ramirez, Zurich (CH)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/632,501

(22) Filed: Jun. 26, 2017

(65) Prior Publication Data

US 2018/0002271 A1 Jan. 4, 2018

(30) Foreign Application Priority Data

Jun. 30, 2016 (EP) ..................... 16177173

(51) Int. Cl.
| | |
|---|---|
| C07C 209/78 | (2006.01) |
| C07C 211/50 | (2006.01) |
| B01J 21/04 | (2006.01) |
| B01J 21/08 | (2006.01) |
| C08G 12/08 | (2006.01) |
| C08G 73/02 | (2006.01) |
| C07C 209/54 | (2006.01) |

(52) U.S. Cl.
CPC ............. *C07C 209/78* (2013.01); *B01J 21/04* (2013.01); *B01J 21/08* (2013.01); *C07C 211/50* (2013.01); *C08G 12/08* (2013.01); *C08G 73/0266* (2013.01); *C07C 209/54* (2013.01)

(58) Field of Classification Search
None
See application file for complete search history.

(56) References Cited

U.S. PATENT DOCUMENTS

| | | | | |
|---|---|---|---|---|
| 3,362,979 A | * | 1/1968 | Bentley | ................ C07C 265/12 521/160 |
| 3,860,637 A | | 1/1975 | Bentley | |
| 3,971,829 A | | 7/1976 | Marquis | |
| 4,039,580 A | | 8/1977 | Frulla et al. | |
| 4,039,581 A | | 8/1977 | Frulla et al. | |
| 4,089,901 A | | 5/1978 | Ziemek et al. | |
| 4,092,343 A | | 5/1978 | Frulla et al. | |
| 4,172,847 A | | 10/1979 | Marquis et al. | |
| 4,294,987 A | | 10/1981 | Prather et al. | |
| 6,649,798 B2 | | 11/2003 | Klein et al. | |
| 6,723,297 B2 | * | 4/2004 | Chen | ....................... B01J 21/12 423/326 |
| 6,936,737 B2 | | 8/2005 | De Angelis et al. | |
| 8,558,027 B2 | | 10/2013 | Weiner et al. | |
| 8,871,979 B2 | | 10/2014 | Mitchell et al. | |
| 2017/0158798 A1 | | 6/2017 | Arras et al. | |

FOREIGN PATENT DOCUMENTS

| | | |
|---|---|---|
| BE | 1013456 A6 | 2/2002 |
| EP | 0264744 A2 | 4/1988 |
| JP | 2012250971 A | 12/2012 |
| WO | 03082803 A1 | 10/2003 |

OTHER PUBLICATIONS

Sosman, R. "The Common Refractory Oxides", Ind. Eng. Chem., 1916, 8(11), 985-990.*
Botella, P. et al; "Towards an industrial synthesis of diamino diphenyl methane (DADPM) using novel delaminated materials: A breakthrough step in the production of isocyanates for polyurethanes"; Applied Catalysis A: General 398; (2011); pp. 143-149; Elsevier.
Brunauer S. et al; "Adsorption of Gases in Multimolecular Layers"; Feb. 1938; pp. 309-319; Bureau of Chemistry and Soils and George Washington University, Washington D.C.
Corma, A. et al; "Preparation, characterisation and catalytic activity of ITQ-2, a delaminated zeolite"; Microporous and Mesoporous Materials; 38; (2000); pp. 301-309; Elsevier.
De Angelis, A. et al; "Solid Acid Catalysts for Industrial Condensations of Ketones and Aldehydes with Aromatics"; Ind. Eng. Chem. Res.; (2004); 43; pp. 1169-1178; American Chemical Society; Published on Web Jan. 28, 2004.
Deutschmann, O. et al; "Heterogeneous Catalysis and Solid Catalysts, 2. Development and Types of Solid Catalysts"; Ullmann's Encyclopedia of Industrial Chemistry; (2012); Wiley-VCH Verlag GmbH & Co. KGaA; Weinheim, Germany.

(Continued)

Primary Examiner — Clinton A Brooks
(74) Attorney, Agent, or Firm — N. Denise Brown

(57) ABSTRACT

The invention relates to a production process for di- and polyamines of the diphenylmethane series by the rearrangement of a condensation product of aniline and a methylene group-supplying agent preferably selected from the group consisting of aqueous formaldehyde solution, gaseous formaldehyde, para-formaldehyde, trioxane and mixtures thereof, wherein said condensation product is reacted in the presence of at least one silica-alumina catalyst, said catalyst having a surface area as determined by the BET method carried out according to ASTM D3663-03 (2015) of from 200 $m^2/g$ to 520 $m^2/g$, preferably of from 350 $m^2/g$ to 495 $m^2/g$, particularly preferably of from 400 $m^2/g$ to 490 $m^2/g$, a molar ratio of silica/alumina on the catalyst surface of A, an overall (bulk) molar ratio of silica/alumina of C, and
a quotient B=A/C;

said catalyst being characterised in that "low" A values (i.e. equal to or lower than 8.0) are combined with "high" B values (i.e. of from 1.50 to 3.00), and "high" A values (i.e. larger than 8.00, especially equal to or larger than 8.50) are combined with "low" B values (i.e. of from 0.15 to 1.40).

17 Claims, No Drawings

(56) References Cited

OTHER PUBLICATIONS

Keller, T. C. et al; "Design of Hierarchical Zeolite Catalysts for the Manufacture of Polyurethane Intermediates"; ACS Catalysis; (2015), 5, pp. 734-743; 2014 American Chemical Society.

Kulkarni, S. J. et al; "The XPS Study of Modified Y Zeolites"; Journal of Catalysis 75, pp. 423-424; (1982); Academic Press, Inc.

Perego, C. et al; "Amorphous aluminosilicate catalysts for hydroxyalkylation of aniline and phenol"; Applied Catalysis; A: General; 307; (2006); pp. 128-136; Available online Apr. 18, 2006; Elsevier.

Salzinger. M. et al; "Reaction network and mechanism of the synthesis of methylenedianiline over dealuminated Y-type zeolites"; Green Chemistry; (2011); 13; pp. 149-155; The Royal Society of Chemistry.

Salzinger, M.; "Catalytic methylenedianiline synthesis on porous solid acids"; Technische Universität München; Lehrstuhl Für Technische Chemie II.; Aug. 25, 2010.

Sanz, J. et al; "Extraframework Aluminum in Steam- and SiCl4-dealuminated Y Zeolite"; J. Chem. Soc.; Faraday Trans. 1; (1988); 84(9); pp. 3113-3119; Published on Jan. 1, 1988.

Wegener, G. et al; "Trends in industrial catalysis in the polyurethane industry"; Applied Catalysis; A:General; 221; (2001); pp. 303-335; Elsevier.

\* cited by examiner

PROCESS FOR THE PRODUCTION OF DI- AND POLYAMINES OF THE DIPHENYLMETHANE SERIES

CROSS-REFERENCE TO RELATED APPLICATION

The present application claims priority under the Paris Convention to European Application No. 16177173.8, filed Jun. 30, 2016, in the European Patent Office the entire contents of which is incorporated herein by reference.

FIELD

The invention relates to a production process for di- and polyamines of the diphenylmethane series by the rearrangement of a condensation product of aniline and a methylene group-supplying agent preferably selected from the group consisting of aqueous formaldehyde solution, gaseous formaldehyde, para-formaldehyde, trioxane and mixtures thereof, wherein said condensation product is reacted in the presence of at least one silica-alumina catalyst, said catalyst having
- a surface area as determined by the BET method carried out according to ASTM D3663-03 (2015) of from 200 m$^2$/g to 520 m$^2$/g, preferably of from 350 m$^2$/g to 495 m$^2$/g, particularly preferably of from 400 m$^2$/g to 490 m$^2$/g,
- a molar ratio of silica/alumina on the catalyst surface of A,
- an overall (bulk) molar ratio of silica/alumina of C, and
- a quotient B=A/C;

said catalyst being characterised in that "low" A values (i.e. equal to or lower than 8.0) are combined with "high" B values (i.e. of from 1.50 to 3.00), and "high" A values (i.e. larger than 8.00, especially equal to or larger than 8.50) are combined with "low" B values (i.e. of from 0.15 to 1.40).

BACKGROUND

Diamines and polyamines of the diphenylmethane series (MDA) are understood to be amines and mixtures of amines of the following formula (I):

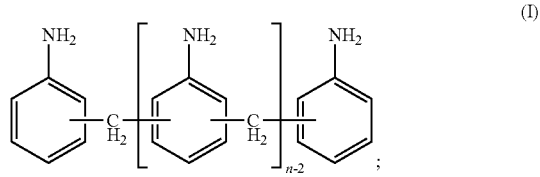

wherein n represents a natural number ≥2.

For compounds and mixtures of compounds with n=2, the term "monomeric MDA" (MMDA) is also conventionally used, whilst compounds and mixtures of compounds with n>2 are conventionally referred to as "polymeric MDA" (PMDA). For the sake of simplicity, mixtures containing compounds with n=2 and n>2 side by side are hereinafter referred to as MDA (diamines and polyamines of the diphenylmethane series). Also for the sake of simplicity, the isomers of MMDA are in the following simply referred to as X,Y'-MDA, X, and Y being numerals indicating the substitution pattern of the two phenylene rings.

The most important isomers of MMDA are 4,4'-MDA, 2,4'-MDA and 2,2'-MDA:

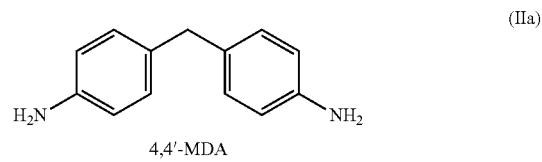
4,4'-MDA (IIa)

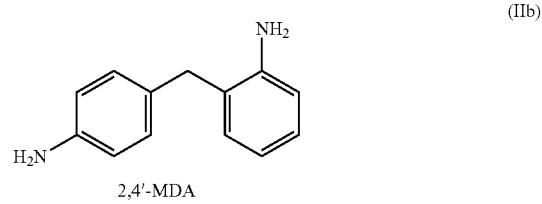
2,4'-MDA (IIb)

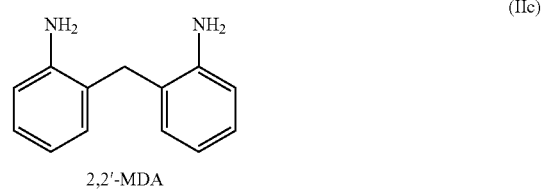
2,2'-MDA (IIc)

4,4'-MDA is sometimes called the para-isomer, whereas both 2,4'-MDA and 2,2'-MDA individually or grouped together are sometimes referred to as ortho-isomers. As a synonym for the PMDA, the terms "higher homologues of MDA" and "oligomers of MDA" can be found in the literature.

MDA is an extremely suitable starting material from which—optionally after further purification—the respective di- and polyisocyanates (hereinafter MDI) that represent an important raw product for polyurethane systems, for example, can be obtained by phosgenation. At the same time, the aliphatic systems that are obtained from MDA by hydrogenation of the aromatic ring also play an important role as paint resins.

Of the many conceivable methods described in the literature for the production of MDA, manufacture from the aniline-formaldehyde condensation product (known as aminal) is the most important because it is the most economically advantageous. This process can be illustrated in idealised form by means of the following diagram:

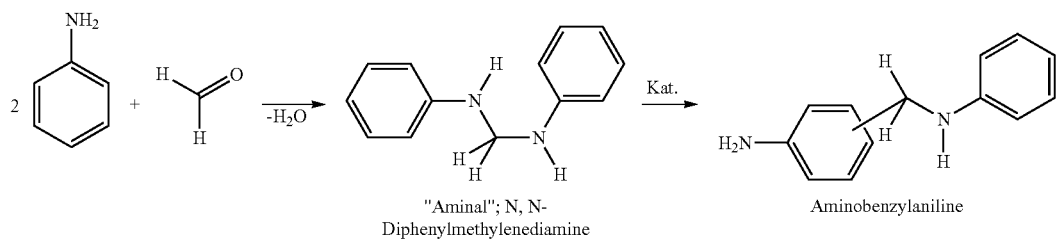

"Aminal"; N, N-Diphenylmethylenediamine

Aminobenzylaniline

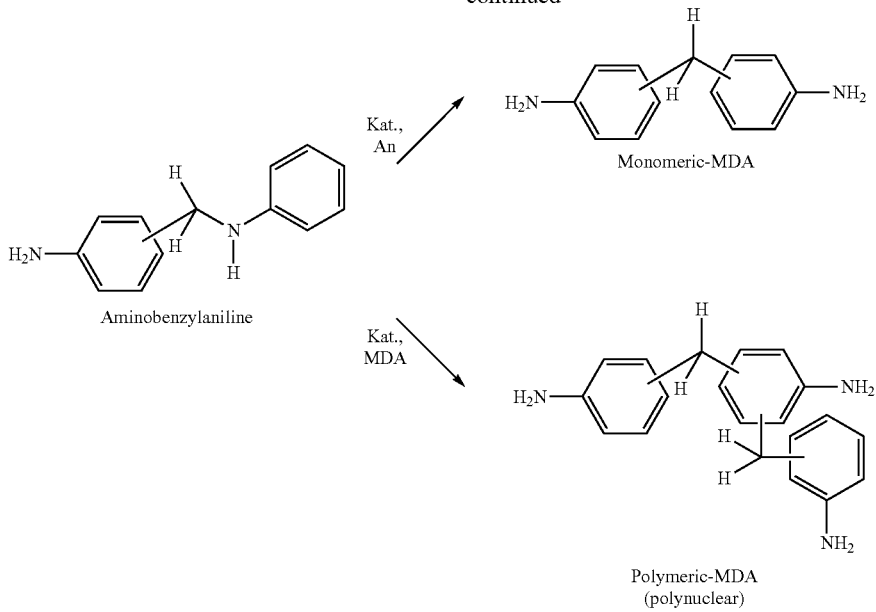

Depending on the variant, the condensation product (the "aminal") is produced first and then rearranged in the presence of a catalyst; alternatively, the condensation itself is performed in the presence of a catalyst under rearrangement conditions.

The rearrangement is catalysed by acids. Usually, solutions of strong acids, such as hydrochloric acid, sulphuric acid, and/or phosphoric acid, are employed in either variant, giving rise to the formation of an amine salt, which generally is subsequently neutralized with a base. For this purpose, strong bases such as sodium hydroxide are frequently used. This process suffers from several disadvantages:

Obviously, large quantities of strong acid are required, which is undesirable from an economic as well as an ecological perspective. In addition, use of strong acids may necessitate use of corrosion resistant materials in the equipment. Such construction materials are often expensive. Furthermore, neutralization of the strong acids employed with bases inevitably leads to the formation of large quantities of salts, which must be disposed of safely. These salts may also be contaminated with organic products, which need to be discharged, resulting in increased production costs. Additionally, substantial quantities of waste water are generated by this process, requiring additional processing capacity for the further treatment of the waste water before this can be safely discharged into a sewerage system.

A whole series of suggestions for the industrial implementation of the rearrangement has therefore already been made in order to overcome these disadvantages. Generally, the approach is taken to substitute mineral acids such as hydrochloric acid by solid acids, thereby simplifying the separation of MDA and catalyst as well as, at least in principle, allowing to re-use the catalyst.

However, a feasible method for the production of MDA avoiding mineral acids must meet the following conditions, for example:

a) Quantitative yields: an intermediate-free (aminobenzylaniline-free) product must be obtained in order to ensure that it is capable of being phosgenated (these can be extremely troublesome in the subsequent processing of the MDA to MDI (phosgenation).

b) Isomer distribution: similarly to the mineral acid-catalysed method, the product composition must be able to be controlled to some extent by varying the process parameters.

c) Service life: a catalyst used in industry must achieve an economic service life with high space-time yields before its activity can be restored by means of regeneration.

d) Foreign substances: the catalyst used must release no trace components in the product that have a negative influence on product quality. In addition, the method must cause no foreign matter, e.g. in the form of a solvent that is foreign to the system, to be brought into the reaction mixture.

Clays such as attapulgite and kaolin are stable up to 180° C. and can be regenerated through calcination (cf U.S. Pat. Nos. 4,039,580, 4,092,343 and 4,294,987). However, in the production of MDA they exhibit a low selectivity to the 4,4'-isomer (the ratio of 4,4'-MMDA to 2,4'-MMDA being approximately of from 2 to 4), as a result of their weak acidity. The intolerance to water in the feed (max. 0.15 wt.-%) is a further drawback in industrial application, since a distillation of the intermediate aminal to reduce the water content is cost-prohibitive.

In contrast, amorphous silica-alumina (ASA) materials provide higher activities, an increased water tolerance (up to 3 wt.-%), and stronger acid sites, leading to improved selectivity, the ratio of 4,4'-MMDA to 2,4'-MMDA being approximately 5 (cf U.S. Pat. Nos. 3,362,979, 3,971,829 and BE 1013456A6). However, an even higher ratio of para to ortho isomers would be desirable.

BE 1013456 A6 describes ASA catalysts exhibiting an overall molar silica:alumina ratio of 10 to 500. Catalysts with a lower overall molar silica:alumina ratio are not described as suitable catalysts for MDA synthesis. BE 1013456 A6 pays no attention at all to the significance of the quotient of the molar silica:alumina ratio on the catalyst surface and the overall (bulk) molar silica:alumina ratio.

ASA catalysts are also mentioned in G. Wegener et al., *Applied Catalysis A: General* (2001) 221, 303-335.

It is known from U.S. Pat. No. 3,860,637 that rearrangement of the aminal using amorphous silicon-aluminium-mixed oxide cracking catalysts results in high yields of 4,4'-isomers when the reaction is performed in the presence of added ortho-isomers. These preferentially react to higher oligomers of MDA. A high proportion of PMDA is therefore conventionally obtained, which has to be separated from the desired 4,4'-isomer. This process requires the additional step of recycling the ortho-isomers initially formed.

DE 2 308 014 A1 describes the synthesis of monomeric MDA over a solid acid catalyst bed in the presence of water. Zeolites, silica-alumina and clays are described as solid catalysts.

U.S. Pat. No. 4,172,847 describes a process for the separation of low functionality substantially pure diaminodiphenylmethanes containing increased 4,4'-isomer contents from methylene-bridged polyphenylpolyamine mixtures prepared by the catalysed condensation reaction of aniline and formaldehyde carried out in the presence of a silica-alumina catalyst. The process is carried out in two steps with the second step below 150° C. Diatomaceous earths, clays and zeolites are described as catalysts.

A general problem of catalysts in MDA synthesis is deactivation due to inefficient removal of reaction products (Alberto de Angelis et al., *Ind. Eng. Chem. Res.*, 2004, 43, 1169-1178). Accordingly, highly mesoporous silica-alumina samples such as MCM-41 have been tested (Carlo Perego et al., *Appl. Catal., A*, 2006, 307, 128-136). However, selectivity was not sufficiently high, and the synthesis of the catalysts is costly.

M. Salzinger describes in *Catalytic methylenedianiline synthesis on porous solid acids* (PhD thesis, Technische Universität München, 2010, Sig. 0001/DM 28664) batch and continuous tests on ordered mesoporous aluminosilicates. It is concluded that non-microporous materials deactivate ca. 10 times slower than microporous zeolites. Catalyst deactivation is attributed to polymeric species on the surface.

M. Salzinger et al. describe in *Reaction network and mechanism of the synthesis of methylenedianiline over dealuminated Y-type zeolites*, Green Chemistry, Vol. 13, No. 1, 2011, 149-155, the results of their investigation on the reaction mechanism of the synthesis of methylenedianiline (MDA) from the condensation product of aniline and formaldehyde (aminal) on microporous acidic materials. The publication does not disclose that the performance of catalysts with a comparatively low molar ratio of silica/alumina on the catalyst surface can be improved if modified such that the quotient of the molar ratio of silica/alumina on the catalyst surface and the overall (bulk) molar ratio of silica/alumina becomes comparatively high.

Jesús Sanz et al. describe in *Extraframework Aluminium in Steam- and SiCl$_4$-dealuminated Y Zeolite*, J. Chem. Soc., Faraday Trans. I, 1998, 84(9), 3113-3119 the results of a study on the dealumination process of a Y zeolite. The publication does not disclose that the performance of catalysts with a comparatively low molar ratio of silica/alumina on the catalyst surface can be improved if modified such that the quotient of the molar ratio of silica/alumina on the catalyst surface and the overall (bulk) molar ratio of silica/alumina becomes comparatively high.

WO 2010/019844 discloses the application of solid acid silica-metal oxide catalysts in the synthesis of MDA. The conversion is below 100% with ABA concentration of >1%. WO 2010/019844 does not disclose that the performance of catalysts with a comparatively low molar ratio of silica/alumina on the catalyst surface can be improved if modified such that the quotient of the molar ratio of silica/alumina on the catalyst surface and the overall (bulk) molar ratio of silica/alumina becomes comparatively high.

Silanized solid materials having a spaciousness index between 2.5 and 19 are disclosed in EP 1 355 874 B1 as catalysts for MDA synthesis. The ratios of 4,4'- to 2,4'-MDA described therein are, depending on the catalyst, between 1.15 and 3.7. Silanization is rather ecologically unfriendly since the utilized precursor tetraorthosilicate have to be produced from pure silicon over silicon tetrachloride as intermediate (Inorganic Silicon Compounds, W. Simmler in Ullmann's Encyclopedia of Industrial Chemistry, 2000, DOI: 10.1002/14356007.a24_001).

EP-A-0 264 744 describes the condensation of aniline with trioxane or free formaldehyde and the rearrangement to MDA using solid boron, titanium and iron-containing zeolites. Simultaneous condensation and rearrangement as well as isolation of aminobenzylanilines with subsequent rearrangement to MDA are both disclosed. Although high monomer selectivity was obtained by rearrangement of the intermediate aminobenzyl anilines to MDA (approx. 90 mol % MMDA in the product after removal of aniline), complete conversion is not achieved. Furthermore the reaction is preferably performed in an additional solvent which is undesirable from an economic perspective.

WO/0158847 A1 describes a process for the production of MDA containing high amounts of MMDA with low ortho-content via a solid acid-catalysed rearrangement of a condensation product from aniline and formaldehyde or another methylene group-supplying agent like trioxane or paraformaldehyde. Preferred solid catalysts are FAU zeolites. The invention is directed at a process which produces an MDA with as little PMDA as possible. However, whilst very high monomer contents might be desirable for certain special applications, it is not desired as a rule in industry to avoid the formation of PMDA since the latter has proven to be useful in many applications. In addition, the process requires the use of highly pure aniline with a very low content of aliphatic amines.

The solid acid catalysed MDA synthesis is reported in JP 2012 250971 A. Silica-alumina and Y zeolites are described as solid catalysts. However, the conversion of the intermediate aminobenzylanilines to MDA is incomplete.

Through delamination of layered, template-containing zeolite precursors through swelling agents and ultrasound, the acid sites can be made accessible to bulkier molecules, and diffusion limitations avoided (Pablo Botella et al., *Appl. Catal., A*, 2011, 398, 143-149, WO 03/082803 A1). The catalytic activity of these zeolites with respect to aminal conversion employing a molar ratio of aniline to formaldehyde (hereinafter "A/F") of 3 is described. The MDA thus obtained contains approximately 25% of PMDA. The exfoliation process results in reduced acid strength compared to zeolitic materials (cf. Avelino Corma et al., *Microporous Mesoporous Mater.*, 2000, 38, 301-309) and thus in a low 4,4'-MDA/2,4'-MDA ratio. Furthermore, this approach is limited to layered zeolites, whose synthesis relies on the application of sacrificial templates and surfactants. The relatively high cost of the zeolites, combined with the excessive consumption of surfactants in the delamination process, render an industrialization of this approach unattractive.

Attempts have also been made to perform the rearrangement of aminal via aminobenzyl aniline to MDA in several steps, for example in two steps, using solid acids in more than one step. U.S. Pat. No. 4,039,581 describes the rearrangement of the aminal using solid acids, whereby the aminal is first dried and then rearranged using zeolites, for example, in several reaction stages with increasing temperature. A temperature of 100° C. is not exceeded. It is assumed that high temperatures in the presence of water would be damaging to selectivity. A full rearrangement of the aminobenzyl aniline intermediates to the MDA cannot be achieved under these conditions. MDA with an MMDA content of approx. 90 mol % in the aniline-free mixture is obtained as product.

WO 2010/072504 A1 describes a continuous process for the synthesis of MDA using solid catalysts. Besides others, different types of silica-alumina as well as clays serve in the first stage to convert aminal towards intermediates like aminobenzylanilines. In the second stage, MMDA and higher homologues are obtained by treating the intermediate mixture with solid catalysts like zeolites, delaminated zeolites or ordered mesoporous materials. The yield of monomeric MDA decreased in general by increasing run-time depending on the choice of catalyst. The necessity of using two different types of catalysts renders the process undesirably complicated.

WO 2016/005269 A1 and T. C. Keller et al., *ACS Catalysis* (2015) 5, 734-743 describe the use of hierarchical zeolite catalysts for MDA synthesis.

To summarise, there has been considerable progress in the area of solid acid catalysis for MDA synthesis. However, up to now no process running with traditional HCl catalysis on a large industrial scale has been replaced by solid acid catalysis, indicating that further improvements in the field of solid acid catalysis are desirable. It would be particularly desirable to provide a solid catalyst with a flexible compositional window that enables the production of various MDA types. Moreover, reproducibility of catalyst performance features and easy scale-up of the catalyst from the laboratory to industrial scale are desirable.

SUMMARY

The invention provides a production process for di- and polyamines of the diphenylmethane series by the rearrangement of a condensation product of aniline and a methylene group-supplying agent preferably selected from the group consisting of aqueous formaldehyde solution, gaseous formaldehyde, para-formaldehyde, trioxane and mixtures thereof, wherein said condensation product is reacted in the presence of at least one silica-alumina catalyst, said catalyst having a surface area as determined by the BET method carried out according to ASTM D3663-03 (2015) of from 200 m²/g to 520 m²/g, preferably of from 350 m²/g to 495 m²/g, particularly preferably of from 400 m²/g to 490 m²/g, a molar ratio of silica/alumina on the catalyst surface of A, an overall (bulk) molar ratio of silica/alumina of C, and a quotient B=A/C;

said catalyst being characterised in that A and B meet the requirements of either Variant I or Variant II recorded in the following tables:

| Variant I | A is of from | | B is of from |
|---|---|---|---|
| | 0.10 to 8.00 | and | 1.50 to 3.00 |
| preferably | 0.15 to 5.00 | and | 1.55 to 2.10 |
| particularly preferably | 0.65 to 4.50 | and | 1.65 to 2.00 |

| Variant II | A is of from | | B is of from |
|---|---|---|---|
| | >8.00 (in particular >8.00 to 100; especially 8.50 to 100) | and | 0.15 to 1.40 |
| preferably | 20.0 to 80.0 | and | 0.35 to 0.95 |
| particularly preferably | 25.0 to 70.0 | and | 0.80 to 0.90 |

DETAILED DESCRIPTION

Within the context of the present invention, the molar ratio of silica/alumina on the catalyst surface (A) corresponds to the molar ratio of silica/alumina as determined by X-ray photoelectron spectroscopy (XPS). For the purpose of determining the ratio A within the meaning of the present invention, XPS is carried out as follows:

Using monochromatic Al Kα radiation by an analyser pass energy of 46.95 eV, the relative abundance of silicon and aluminium is obtained by the different peak areas using built-in PHI sensitivity factors. The general principle of XPS on silica-alumina materials can be found in S. J. Kulkarni et al., *Journal of Catalysis*, Volume 75, Pages 423 to 424 (1982).

Within the context of the present invention, the overall (bulk) molar ratio of silica/alumina (C) corresponds to the molar ratio of silica/alumina as determined by inductively coupled plasma optical emission spectroscopy (ICP-OES).

For the purpose of determining the ratio C within the meaning of the present invention, ICP-OES is carried out as follows:

The amount of silicon and aluminium in the solid catalyst is determined by ICP-OES (preferably, using a Horiba Ultima 2 instrument equipped with photomultiplier tube detection which was used in all examples given below). Samples (ca. 50 mg) are dissolved in HF (0.50 cm³) and HNO₃ (3.0 cm³) and diluted with saturated boric acid solution (30 cm³). Then, the samples are further diluted with water to attain concentrations in the range of 5.0 to 50 ppm of the element of interest (Si, Al) and measured with a 5-point calibration curve.

The quotient of A and C is referred to as B in the present invention.

A and B meeting the requirements of either Variant I or Variant II as set forth in the tables above means that, exemplified for the broadest range of each variant, in Variant I, A is from 0.10 to 8.00 and B is from 1.50 to 3.00, and in Variant II, A is >8.00 and B is from 0.15 to 1.40.

Surprisingly, it has been discovered that the performance properties of catalyst with "low" C values (which were hitherto believed to be unsuitable for MDA synthesis; see, for example, BE 1013456 A6, describing a minimum C value of 10 for successful catalysts) can be significantly improved by the method according to the invention. Generally, at least by trend, "low" C values correspond to "low"

A values. It has now been found that the performance properties of catalysts with "low" A values can be significantly improved if combined with "high" B values. On the other hand, even for catalysts with "high" A value, hitherto—in principle—known as being suitable for MDA synthesis, especially good catalyst performance was observed if those catalysts have "low" B values. Without wishing to be bound by a theory, it is believed that the combination of "low" A values with "high" B values (Variant I) and the combination of "high" A values with "low" B values (Variant II) improves the catalyst properties in that attained porosity and Brønsted acidity is enhanced compared to the bulk material, as will be described in more detail below. No such observation has been made in the prior art previously.

A brief summary of various possible embodiments of the invention firstly follows:

In a first embodiment of the invention, which can be combined with any other embodiment except those embodiments exclusively directed at catalysts having a core-shell structure, the at least one silica-alumina catalyst is derived from co-precipitation of a water-soluble aluminium precursor and a water-soluble silicon precursor.

In a second embodiment of the invention, which is a particular variant of the first embodiment, the water-soluble aluminium precursor is an alkali metal aluminium salt, preferably selected from the group consisting of sodium aluminate, potassium aluminate, sodium aluminium sulphate and potassium aluminium sulphate and the water-soluble silicon precursor is an alkali metal silicon salt, preferably selected from the group consisting of sodium silicates and potassium silicates.

In a third embodiment of the invention, which is a particular variant of the first or second embodiment, the co-precipitation is carried out in the presence of a precipitating agent selected from the group consisting of mineral acids and carboxylic acids, preferably from the group consisting of oxalic acid, nitric acid, sulphuric acid and hydrochloric acid.

In a fourth embodiment of the invention, which can be combined with any other embodiment except those embodiments exclusively directed at catalysts prepared by co-precipitation, the at least one silica-alumina catalyst has a core-shell structure.

In a fifth embodiment of the invention, which is a particular variant of the forth embodiment, the core of the at least one silica-alumina catalyst comprises an aluminium species selected from the group consisting of aluminium oxides, aluminium oxide hydroxides and aluminium hydroxides, preferably from the group consisting of γ-$Al_2O_3$ and boehmite.

In a sixth embodiment of the invention, which is a particular variant of the fifth embodiment, the at least one silica-alumina catalyst is derived from precipitation of a water-soluble silicon precursor onto the core, the water-soluble silicon precursor preferably being an alkali metal silicon salt, particularly preferably selected from the group consisting of sodium silicates and potassium silicates.

In a seventh embodiment of the invention, which is a particular variant of the sixth embodiment, the precipitation is carried out in the presence of a precipitating agent selected from the group consisting of mineral acids and carboxylic acids, preferably selected from the group consisting of oxalic acid, nitric acid, sulphuric acid and hydrochloric acid.

In an eighth embodiment of the invention, which is a particular variant of the forth embodiment of the invention, the core of the at least one silica-alumina catalyst comprises a silicon species selected from the group consisting of silica and mesoporous silica.

In a ninth embodiment of the invention, which is a particular variant of the eight embodiment of the invention, the at least one silica-alumina catalyst is derived from precipitation of a water-soluble inorganic aluminium precursor onto the core, the water-soluble inorganic aluminium precursor preferably being selected from the group consisting of aluminium nitrate, aluminium sulphate and aluminium halides.

In a tenth embodiment of the invention, which is a particular variant of the ninth embodiment of the invention, the precipitation is carried out in the presence of an alkaline precipitating agent, preferably selected from the group consisting of alkali hydroxides, ammonia solution and compounds that decompose under release of a base.

In an eleventh embodiment of the invention, which is a particular variant of the tenth embodiment of the invention, the alkaline precipitating agent comprises urea.

In a twelfth embodiment of the invention, which is a particular variant of the eight embodiment of the invention, the at least one silica-alumina catalyst is derived from the hydrolysis of an organic aluminium precursor onto the core.

In a thirteenth embodiment of the invention, which is a particular variant of the twelfth embodiment of the invention, the organic aluminium precursor is selected from the group consisting of aluminium isopropoxide, aluminium acetate and aluminium lactate.

In a fourteenth embodiment of the invention, which can be combined with any other embodiment, the process is carried out according to variant I, i.e. A and B meet the following requirements:

A is of from Bis of from
0.10 to 8.00 and 1.50 to 3.00;
preferably 0.15 to 5.00 and 1.55 to 2.10;
particularly 0.65 to 4.50 and 1.65 to 2.00;
preferably The embodiments which have been briefly indicated above and further possible variants of the invention are explained in more detail in the following. Individual embodiments can be combined with each other unless the contrary is obvious for the person skilled in the art.

Methylene group-supplying agents which can be used in the process for the preparation of di- and polyamines of the diphenylmethane series according to the invention include aqueous formaldehyde solution, gaseous formaldehyde, para-formaldehyde, trioxane and mixtures thereof. Aqueous formaldehyde solution is particularly preferred. For the process of the present invention, preferably aqueous formaldehyde of technical quality having a formaldehyde concentration of 30% by weight to 50% by weight is used; typically this technical formaldehyde solution contains methanol in a 0.1% by weight to 15% by weight range. It is also possible to use aqueous formaldehyde solutions which have a lower or a higher formaldehyde concentration than mentioned before.

For the process according to the invention, aniline grades are preferably used that are largely free from aliphatic amines as minor and trace constituents (e.g. cyclohexylamine, dicyclohexylamine). For the process according to the invention, aniline with a purity of ≥99.5% is preferably used. In this context, the purity of the aniline refers to the purity of aniline freshly introduced into the process from an outside source ("fresh aniline"). As is well known in the art, the aniline which, in a process on an industrial scale, is actually reacted with the methylene group-supplying agent is usually a mixture of such "fresh aniline" and aniline streams which have been recycled from other parts of the process, the latter usually being less pure.

The process according to the invention is preferably performed in the absence of solvents.

In a preferred embodiment of the invention, the methylene group-supplying agent is reacted with aniline in the absence of an acidic catalyst, whereby a (condensation) product is formed that can be given the alternative name of aminal and consists predominantly of N,N'-diphenyl-methylenediamine. This condensation product is preferably separated from the water of reaction when using aqueous formaldehyde solution, gaseous formaldehyde or mixtures thereof with the other methylene group-supplying agents mentioned before by phase separation and may further be dehydrated before the further reaction is performed under catalysis, although such an additional dehydration step is not strictly necessary and can be dispensed with.

In principle, the reaction of aniline and the methylene group-supplying agent to give the aminal can be performed also in the presence of a catalyst that causes the rearrangement to aminobenzylaniline (ABA) and/or the MDA isomers. However, the water that is released during the condensation reaction when using aqueous formaldehyde solution, gaseous formaldehyde or mixtures thereof with the other methylene group-supplying agents mentioned before reduces the activity and selectivity of the catalyst, as a consequence of which the successive version (aminal reaction→phase separation→rearrangement) is preferred.

The aminal reaction is preferably performed continuously by metering aniline and formaldehyde solution in a molar ratio of aniline to formaldehyde of 1.7 to 100, preferably 1.8 to 50, particularly preferably 2.0 to 20, into a reactor, from which a reaction quantity of the same volume as the feed stream is continuously removed and sent for phase separation. A batchwise or semi-continuous process is also conceivable, whereby the aniline and formaldehyde are metered in the desired mixing ratio into a stirred batch reactor, from which the aminal that is reacted out is then sent for drying.

The desired molar ratio of aniline to formaldehyde (A/F) for the rearrangement can be set at the time of the aminal reaction, optionally taking the drying losses into consideration. In principle, however, it is also possible to perform the aminal reaction at a lower molar ratio of A/F as desired and then to set the desired value immediately before the rearrangement using pure, dry aniline. The latter option allows the use of smaller apparatus at the aminal reaction and drying stages, leading to lower investment costs. Aniline recovered from reprocessing of the reaction mixture (recycled aniline) can also be used for restocking after condensation, which in the case of the operation using an excess of aniline is recovered from the fully rearranged MDA.

The rearrangement can preferably be performed batchwise or continuously in a stirred-tank reactor, a series of stirred-tank reactors, in a tubular reactor (e.g. fixed-bed or fluidised-bed reactor) or in a combination thereof. Serial fixed catalyst beds are advantageously used. A mixture of aminobenzylanilines, aniline and small quantities of diaminophenylmethanes is preferably first obtained in a temperature range of 20° C. to 70° C., particularly preferably 40° C. to 60° C., depending on the catalyst used. To this end, the reaction mixture is preferably pumped over the fixed catalyst bed, whereby residence times of 0.20 to 2.0 hours are typically set. The optimum temperature for a selected catalyst and a desired isomer ratio in the aminobenzylanilines obtained is easily determined by means of preliminary tests.

The reaction to MDA is completed using the same or another catalyst bed at an increased temperature of 70° C. to 200° C., particularly preferably of 70° C. to 160° C., whereby residence times of 0.20 hours to 48 hours, preferably 0.50 hours to 24 hours, particularly preferably 1.0 hour to 18 hours are typically set. The phrase "another catalyst bed" can describe either another catalyst bed having the same composition than the first catalyst bed, or another catalyst bed based on a different catalyst composition than the first catalyst bed or a combination thereof.

On completion of the reaction, the reaction mixture obtained by the process according to the invention and after separation from the catalyst can be processed such that the excess aniline optionally contained in the mixture can be separated from the MDA isomers either continuously or batchwise by known methods such as distillation or crystallisation, for example, and recycled. The MDA isomers are then preferably sent for subsequent phosgenation.

The silica-alumina catalysts used according to the invention are amorphous silica-alumina catalysts (ASA catalysts). Within the context of the present invention, "amorphous" means that x-ray diffraction does not evidence any diffraction patterns or, in case of core-shell catalysts, only possible diffraction patterns of the support (i.e. the core). Silica-alumina catalysts that meet this requirement are called "X-ray amorphous" catalysts in the following. For the purpose of determining whether or not a catalyst is amorphous in this sense, X-ray diffraction is carried out using Ni-filtered Cu Kα radiation. The patterns are recorded in the 2θ range of 5° to 70° on a diffractometer.

In the process according to the invention, silica-alumina catalysts having a surface area as determined by the BET method of from 200 m$^2$/g to 520 m$^2$/g, preferably of from 350 m$^2$/g to 495 m$^2$/g, particularly preferably of from 400 m$^2$/g to 490 m$^2$/g, are used. The BET method was first described in 1938 (S. Brunauer, P. H. Emmett, E. Teller, *J. Am. Chem. Soc.* (1938) 60, 309-319. For the purpose of determining the catalyst surface area within the meaning of the present invention, the BET method is carried out according to ASTM D3663-03 (2015).

In principle, there are two preferred methods of preparing the silica-alumina catalysts to be used in the process of the invention:

(1) Co-precipitation of a silicon and aluminium precursor, and (2) Application of a precursor of either silicon or aluminium onto a core substantially or completely consisting of a component of the respective other element, resulting in a catalyst having a shell rich in either silicon or aluminium that is applied onto a core rich in the respective other element.

Preparing catalysts according to method (1) is preferably carried out by co-precipitating a water-soluble aluminium precursor and a water-soluble silicon precursor. "Water-soluble" in this context means that the silicon and aluminium precursors in their solid states can be dissolved in water at room temperature; the term "water-soluble" as used in this invention does, however, not imply solubility without any decomposition.

Preferred aluminium precursors are alkali metal aluminium salts with sodium aluminate, potassium aluminate, sodium aluminium sulphate and/or potassium aluminium sulphate being particularly preferred. Preferred silicon precursors are alkali metal silicon salts with sodium silicates and potassium silicates being particularly preferred.

Suitable precipitating agents used in method (1) are mineral acids and carboxylic acids, which are preferably selected from the group consisting of oxalic acid, nitric acid, sulphuric acid and hydrochloric acid. Preferably, starting from a strongly basic environment (i.e. pH >11.0), the pH is lowered to a value of from 7.0 to 10.8, particularly preferably of from 9.0 to 10.5.

Preferably, the silicon and aluminium precursors are used in aqueous solutions resulting in a theoretical yield of silica-alumina in the range of from 20.0 $g_{metal\ oxide}$/L to 200 $g_{metal\ oxide}$/L, preferably of from 50.0 $g_{metal\ oxide}$/L to 150 $g_{metal\ oxide}$/L, particularly preferably of from 90.0 $g_{metal\ oxide}$/L to 110 $g_{metal\ oxide}$/L. A loading typically used is 100 $g_{metal\ oxide}$/L, "metal oxide" referring to the sum of $Al_2O_3$ and $SiO_2$. The precursor solutions are mixed at a temperature in the range of from 20.0° C. to 100° C. Applying the precipitating agents, especially the above mentioned mineral acids in concentrations in the range of 0.10 mol/L to 2.0 mol/L, the catalyst precipitates.

Method (2) is, however, preferred. The catalysts prepared by this method are commonly referred to as core-shell catalysts or egg-shell catalysts (the terms are used synonymously in the literature and within the meaning of the present invention). Such catalysts are inter alia described in Ullmann's Encyclopedia of Industrial Chemistry, 2012, Heterogeneous Catalysis and Solid Catalysts, 2. Development and Types of Solid Catalysts, Wiley-VCH Verlag GmbH & Co. KGaA, Weinheim, see especially page 502 and page 528; DOI: 10.1002/14356007.o05_o02. Catalysts having a core- (or egg-)shell structure within the meaning of this invention are understood as consisting of an outer layer of a catalytically-active phase applied onto an inner support (the core) which is of lower catalytic activity than the outer layer (or which is even inert). Egg-shell type or core-shell type catalysts are also referred to as coated catalysts in the literature.

The core can be either rich in aluminium or rich in silicon:

In the first case, the core preferably comprises (more preferably consists of) an aluminium species selected from the group consisting of aluminium oxides, aluminium oxide hydroxides and aluminium hydroxides, $\gamma$-$Al_2O_3$ and boehmite being most preferred. The core-shell structure is preferably established by applying a water-soluble silicon precursor onto the core by precipitation, particularly by lowering the pH starting from a neutral or basic environment. As regards the term "water-soluble", the same applies what was said above, i.e. "water-soluble" means that the silicon precursor in its solid state can be dissolved in water at room temperature, however, not necessarily without any decomposition. Preferred silicon precursors are alkali metal silicon salts, with sodium silicates and potassium silicates being particularly suitable.

Suitable precipitating agents used in this first case are mineral acids and carboxylic acids, which are preferably selected from the group consisting of oxalic acid, nitric acid, sulphuric acid and hydrochloric acid.

In the second case (i.e. core rich in silicon), the core preferably comprises (more preferably consists of) a silicon species selected from the group consisting of silica and mesoporous silica. The core-shell structure is preferably established by applying a water-soluble inorganic aluminium precursor onto the core by precipitation. Again, the term "water-soluble" means that the inorganic aluminium precursor in its solid state can be dissolved in water at room temperature, however, not necessarily without any decomposition. Preferred inorganic aluminium precursors are selected from the group consisting of aluminium nitrate, aluminium sulphate, and aluminium halides.

Suitable precipitating agents used in this second case are alkaline substances (i.e substances which increase the pH value), and are preferably selected from the group consisting of alkali hydroxides, ammonia solution and compounds that decompose under release of a base. A preferred example of the latter is urea, which releases ammonia.

In a variant of method (2), second case, an organic aluminium precursor is applied to a core rich in silicon by hydrolysis of said organic aluminium precursor onto the silicon-rich core. The organic aluminium precursor is preferably selected from the group consisting of aluminium isopropoxide, aluminium acetate and aluminium lactate.

In both methods, (1) and (2), freshly prepared catalyst is preferably subjected to calcination, particularly preferably in static air at a temperature of from 300° C. to 800° C., preferably from 400° C. to 600° C., for a time of from 5.0 minutes to 24 hours, preferably from 30 minutes to 5.0 hours.

Regardless of the method used to prepare the catalyst, it must be ensured that the requirements for the quotient B are in combination with the ratio A are met.

For method (1) (i.e. catalysts prepared by co-precipitation), the requirements of the invention regarding the parameters A and B can preferably be achieved by lowering the pH value at the end of the precipitation step to a value of from 7.0 to 10.8, particularly preferably of from 9.0 to 10.5. In doing so, it is ensured that the precursors precipitate, and in particular precipitate one after the other or at least with a time delay, and do not dissolve again. More particularly, in a preferred embodiment the precursors precipitate first into an Al-enriched (when compared to the bulk ratio) core which is subsequently covered by an Al-depleted (when compared to the bulk ratio) layer, and no dissolution of precipitated species occurs.

For method (2) (i.e. core-shell catalysts), the requirements of the invention regarding the parameters A and B can preferably be achieved by selecting appropriate ratios of the respective precursors in catalyst preparation. To this end, the skilled person can start with theoretical values derived from simple stoichiometric calculations, verifying the result by applying the XPS and ICP-OES measurements described above. A few preliminary tests modifying the values derived from the initial stoichiometric calculations may be necessary in some cases, however, finally arriving at catalysts meeting the requirements of the invention poses no principal difficulty for the skilled person.

As previously stated, without wishing to be bound by a theory, it is believed that the combination of "low" A values with "high" B values (Variant I) and the combination of "high" A values with "low" B values (Variant II) improves the catalyst properties in that attained porosity and Brønsted acidity is enhanced compared to the bulk material. Specifically, the acidity of a catalyst can be decoupled from its porosity allowing a broader flexibility in the choice of the materials. This is demonstrated in that the catalysts to be used according to the invention exhibit considerably lower BET surfaces than previously believed to be possible.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

I. Preparation of Aminal

In a four-neck round-bottom flask charged with nitrogen, 150 g aniline were added and heated under stirring to a temperature of 80° C. Then, a further portion of 315.7 g aniline as well as 134 g of aqueous formaldehyde solution (37.1 wt.-% HCHO) were added dropwise via separate dropping funnels within 20 minutes. The suspension thus obtained was further stirred for 10 minutes and in the next step transferred to an evacuated separation funnel, in which the suspension was allowed to settle for 20 minutes. The aqueous phase was separated from the aminal phase, whereby the latter one was used as starting material for the catalytic runs described in the following examples.

II. Preparation of Catalyst

II.0 Commercial ASA Catalysts:

Four commercial catalysts were obtained from SASOL ("SIRAL® 10, SIRAL® 20, SIRAL® 30, SIRAL® 40"—a, b, c, and d).

II.1 ASA Catalysts by Homogeneous Deposition Precipitation of $Al(NO_3)_3$ onto $SiO_2$:

A 250 mL flask was charged with 150 mL of water, 5.00 g of $SiO_2$ (Silicagel, Sigma Aldrich), the desired amount of $Al(NO_3)_3 \cdot 9H_2O$ (0.950 g or 1.95 g) and 7.20 g of Urea, and stirred at 90° C. for 6.0 h. Then, the solids were filtered off, washed three times with ca. 50 mL of water, and dried at 65° C. for 12 h. Calcination in static air was carried out at 550° C. for 5.0 h with a ramp rate of 2.5° C. $min^{-1}$.

The variation in aluminium concentration resulted in two different catalysts, a and b.

II.2 ASA Catalysts by Co-Precipitation of Sodium Aluminate and Sodium Silicate:

Sodium silicate (26.5% $SiO_2$) was diluted to 100 mL with deionized water. Then, a solution of sodium aluminate in 100 mL water was added, and the mixture dispersed with an IKA Ultra-Turrax T25 disperser at 9500 rpm for 5.0 min and left ca. 10 min for gelation, before it was re-dispersed. The concentration of the silica and alumina source were adapted to attain the desired composition, while maintaining an oxide loading of 50 g $L^{-1}$. A beaker equipped with a disperser at 9500 rpm was charged with 50 mL $H_2O$, and then 30 mL $min^{-1}$ of the gel and ca. 20 to 30 mL $min^{-1}$ of 0.50 M $HNO_3$ were simultaneously added. The acid flowrate is adapted to ensure a pH between 9.7 and 9.9 during the precipitation. The gel was filtered and ion-exchanged three times with 0.5 L of 0.50 M $NH_4NO_3$ for 8.0 h, re-dispersed in 250 mL water and pumped at 3.0 $cm^3$ $min^{-1}$ into a Büchi Mini Spray Dryer B-290 equipped with a two-fluid nozzle of 1.4 mm diameter together with a spray air flow of 0.50 $m^3$ $h^{-1}$. The inlet temperature was set at 493° K, the aspiration rate at 35 $m^3$ $h^{-1}$, and the outlet temperature at 383° K. The dried particles were separated by using a cyclone and calcined at 550° C. in static air with a ramp rate of 2.5° C. $min^{-1}$.

The variation in aluminium concentration resulted in two different catalysts, a and b.

II.3 ASA Catalysts by Isopropoxide Grafting:

5.00 g of $SiO_2$ (Silicagel, Sigma Aldrich, 'high' (II.3a) or Silica nanoparticles 10-20 nm 99.5%, Sigma Aldrich, 'low' (II.3b) was evacuated overnight at 60° C. in a round bottom flask. The flask was charged with 50 mL of isopropanol and 0.50 g or 1 g of aluminium isopropoxide and refluxed for 5.0 h. Then, the solids were filtered off, washed three times with ca. 50 mL of isopropanol, and dried at 65° C. for 12 h. Calcination in static air was carried out at 550° C. for 5 h with a ramp rate of 2.5° C. $min^{-1}$.

By varying silica as well as alumina precursor concentration, a 2×2 matrix (catalysts a, b, c and d) was obtained for catalytic testing.

III. Catalytic Tests

The reaction conditions for the catalytic tests were deliberately selected to attain a partial rearrangement of the intermediate species, enabling a comparison of activity and selectivity.

For running the catalytic experiments, a multi-batch reactor system (AMTEC, SPR-16) was used consisting of 16 parallel reactors with a volume of 15 mL each. Each reactor was pressurized with nitrogen, filled with the respective zeolite (0.10 g to 1.00 g) and aminal (4.90 g). Agitation was achieved via magnetic stirring at 500 rpm and the system was heated up to a temperature of 140° C. After a reaction time of 1.0 h, the reactors were cooled to room temperature. The suspension was filtered through a syringe filter and an aliquot from the filtrate was taken for HPLC analysis (Agilent 1100 Series), for which a mixture of methanol, water and acetonitrile was used as eluent and a phenomenex column as stationary phase. Applying a method with external 3-point calibration, the components mentioned in the next examples could be quantified. Prior to injection, the respective aliquot (approximately 50 mg) was diluted in an N-ethyldiisopropylamine solution of 50 mL (0.12% w/w in methanol/THF solution (1:2 w/w)) and transferred in a vial. A/F ratio was kept constant in all experiments.

The yields of 4,4'-MDA, 2-nuclear ABAs ("nuclear" designating the number of phenylene rings), 2-nuclear MDA, 3-nuclear MDA and residual aniline are displayed in the following; "yield" referring to wt.-% of the total weight of the resulting reaction mixture. The difference to 100 wt.-% consists predominantly or exclusively of higher-nuclear (i.e. 4 or more phenylene rings) MDA structures.

| Catalyst | Variant | Ratio A [XPS] | Quotient B [= A/C] | Ratio C [ICP-OES] | $S_{BET}$* $m^2/g$ | Yield of 4,4'-MDA wt.-% | Yield of 2-nuclear ABAs wt.-% | Yield of 2-nuclear MDA wt.-% | Yield of 3-nuclear MDA wt.-% | Residual Aniline wt.-% |
|---|---|---|---|---|---|---|---|---|---|---|
| II.0.a (comp.) | — | 0.21 | 1.11 | 0.19 | 385 | 3 | 34 | 3 | <1 | 42 |
| II.0.b | I | 0.62 | 1.59 | 0.39 | 429 | 8 | 28 | 9 | <1 | 39 |
| II.0.c | I | 1.32 | 1.81 | 0.73 | 474 | 16 | 19 | 19 | 2 | 40 |
| II.0.d | I | 2.09 | 1.85 | 1.13 | 512 | 22 | 15 | 26 | 3 | 39 |
| II.1.a | II | 32.0 | 1.08 | 29.7 | 406 | 25 | 12 | 30 | 4 | 39 |
| II.1.b | II | 51.7 | 0.83 | 62.6 | 433 | 24 | 12 | 29 | 4 | 39 |
| II.2.a (comp.) | — | 5.6 | 1.27 | 4.4 | 311 | 19 | 17 | 23 | 3 | 40 |
| II.2.b | II | 14.3 | 1.32 | 10.8 | 403 | 26 | 11 | 32 | 4 | 39 |
| II.3.a | II | 10.2 | 0.43 | 23.6 | 454 | 16 | 21 | 20 | 2 | 30 |
| II.3.b | II | 8.9 | 0.19 | 48.1 | 481 | 12 | 24 | 15 | 1 | 32 |

-continued

| Catalyst | Variant | Ratio A [XPS] | Quotient B [= A/C] | Ratio C [ICP-OES] | $S_{BET}$* $m^2/g$ | Yield of 4,4'-MDA wt.-% | Yield of 2-nuclear ABAs wt.-% | Yield of 2-nuclear MDA wt.-% | Yield of 3-nuclear MDA wt.-% | Residual Aniline wt.-% |
|---|---|---|---|---|---|---|---|---|---|---|
| II.3.c (comp.) | — | 20.0 | 0.76 | 26.4 | 131 | 8 | 29 | 10 | <1 | 40 |
| II.3.d (comp.) | — | 34.6 | 0.68 | 50.6 | 146 | 6 | 31 | 7 | <1 | 32 | comp. = comparison;
ABA = aminobenzylaniline
*$S_{BET}$ surface area of catalyst as determined by BET method carried out according to ASTM D3663-03 (2015)

The invention claimed is:

1. A process for the preparation of di- and polyamines of the diphenylmethane series comprising rearranging a condensation product of aniline and a methylene group-supplying agent, wherein said condensation product is reacted in the presence of at least one silica-alumina catalyst, wherein said catalyst has (i) a surface area as determined by the BET method carried out according to ASTM D3663-03 (2015) of from 200 $m^2/g$ to 520 $m^2/g$; (ii) a molar ratio of silica/alumina as determined by X-ray photoelectron spectroscopy of A; and (iii) a quotient B equal to (the molar ratio of silica/alumina as determined by X-ray photoelectron spectroscopy) divided by (the molar ratio of silica/alumina as determined by inductively coupled plasma optical emission spectroscopy); in which A and B of the catalyst meet one of the following requirements: either (I) A is of from 0.10 to 8.00 and B is of from 1.50 to 3.00, or (II) A is >8.00 and B is of from 0.15 to 1.40.

2. The process according to claim 1, wherein said at least one silica-alumina catalyst is prepared by co-precipitating a water-soluble aluminium precursor and a water-soluble silicon precursor.

3. The process according to claim 2, wherein said water-soluble aluminium precursor comprises an alkali metal aluminium salt and the water-soluble silicon precursor comprises an alkali metal silicon salt.

4. The process according to claim 2, wherein the co-precipitation is carried out in the presence of a precipitating agent which is selected from the group consisting of mineral acids and carboxylic acids.

5. The process according to claim 1, wherein said at least one silica-alumina catalyst has a core-shell structure.

6. The process according to claim 5, wherein the core of said at least one silica-alumina catalyst comprises an aluminium species which is selected from the group consisting of aluminium oxides, aluminium oxide hydroxides and aluminium hydroxides.

7. The process according to claim 6, wherein said at least one silica-alumina catalyst is prepared by precipitating a water-soluble silicon precursor onto the core.

8. The process according to claim 7, wherein the precipitation is carried out in the presence of a precipitating agent which is selected from the group consisting of mineral acids and carboxylic acids.

9. The process according to claim 5, wherein the core of said at least one silica-alumina catalyst comprises a silicon species which is selected from the group consisting of silica and mesoporous silica.

10. The process according to claim 9, wherein said at least one silica-alumina catalyst is prepared by precipitating a water-soluble inorganic aluminium precursor onto the core.

11. The process according to claim 10, wherein the precipitation is carried out in the presence of an alkaline precipitating agent.

12. The process according to claim 11, wherein said alkaline precipitating agent comprises urea.

13. The process according to claim 9, wherein said at least one silica-alumina catalyst is prepared by hydrolysing an organic aluminium precursor onto the core.

14. The process according to claim 13, wherein said organic aluminium precursor is selected from the group consisting of aluminium isopropoxide, aluminium acetate and aluminium lactate.

15. The process according to claim 1, wherein A and B of the catalyst meet the requirements of (I).

16. The process according to claim 1, wherein A is of from 0.15 to 5.00 and B is of from 1.55 to 2.10.

17. The process according to claim 1, wherein A is of from 0.65 to 4.50 and B is of from 1.65 to 2.00.

* * * * *